United States Patent [19]

Audon et al.

[11] Patent Number: 5,054,044
[45] Date of Patent: Oct. 1, 1991

[54] RADIOLOGY INSTALLATION WITH A COMMUNICATIONS NETWORK

[75] Inventors: Philippe Audon, La Celle St. Cloud; Daniel Courtecuisse, Auffargis, both of France

[73] Assignee: Thomson-CGR, Paris, France

[21] Appl. No.: 355,818

[22] Filed: May 16, 1989

Related U.S. Application Data

[63] Continuation of Ser. No. 45,872, May 4, 1987, abandoned.

[30] Foreign Application Priority Data

May 6, 1986 [FR] France .................. 86 06546

[51] Int. Cl.$^5$ ............................................. H05G 1/08
[52] U.S. Cl. ..................................... 378/91; 378/116; 370/85.12
[58] Field of Search ................. 340/825.05; 370/86, 370/85.12; 358/111; 378/91, 99, 116, 115

[56] References Cited

U.S. PATENT DOCUMENTS

| | | | |
|---|---|---|---|
| 3,783,251 | 1/1974 | Pavkovich | 378/196 |
| 4,211,927 | 7/1980 | Hellstrom et al. | 378/91 |
| 4,533,947 | 8/1985 | Smith | 378/99 |
| 4,544,948 | 10/1985 | Okazaki | 358/111 |
| 4,596,982 | 6/1986 | Bahr et al. | 340/825.05 |
| 4,731,784 | 3/1988 | Keller et al. | 370/88 |
| 4,741,015 | 4/1988 | Charrier | 378/196 |
| 4,829,516 | 5/1989 | Orimo et al. | 370/85.12 |

FOREIGN PATENT DOCUMENTS

| | | |
|---|---|---|
| 0066928 | 12/1982 | European Pat. Off. . |
| 0136645 | 4/1985 | European Pat. Off. . |
| 0192795 | 9/1986 | European Pat. Off. ............ 370/86 |
| 2115876 | 7/1972 | France . |
| 2247871 | 5/1975 | France . |
| 2354017 | 12/1977 | France . |

OTHER PUBLICATIONS

"A Microprocessor-Based Controller for a Loop Switching System" by Anderson et al., Int. Conf. on Communications, Jun. 1978.
"Overlay Optical-Fiber Local Area Network" by Keller et al., IEEE 85-80023 Dec. 1985, pp. 1185-1189.
"A Local Communications Network ... Token Access Rings: A Tutorial" by Strole, IBM J. Res. DEvelop. vol. 27, #5, 9/1983, pp. 481-497.

Primary Examiner—Carolyn E. Fields
Assistant Examiner—David P. Porta
Attorney, Agent, or Firm—Oblon, Spivak, McClelland, Maier & Neustadt

[57] ABSTRACT

Radiology installation comprising a set of instruments between which there is a flow of data signals. For the transmission of these signals, the installation comprises at least two loops between which the data can flow. Each loop is capable of transmitting data which does not flow through another loop. Preferably, there is a main loop and secondary or specialized loops.

15 Claims, 3 Drawing Sheets

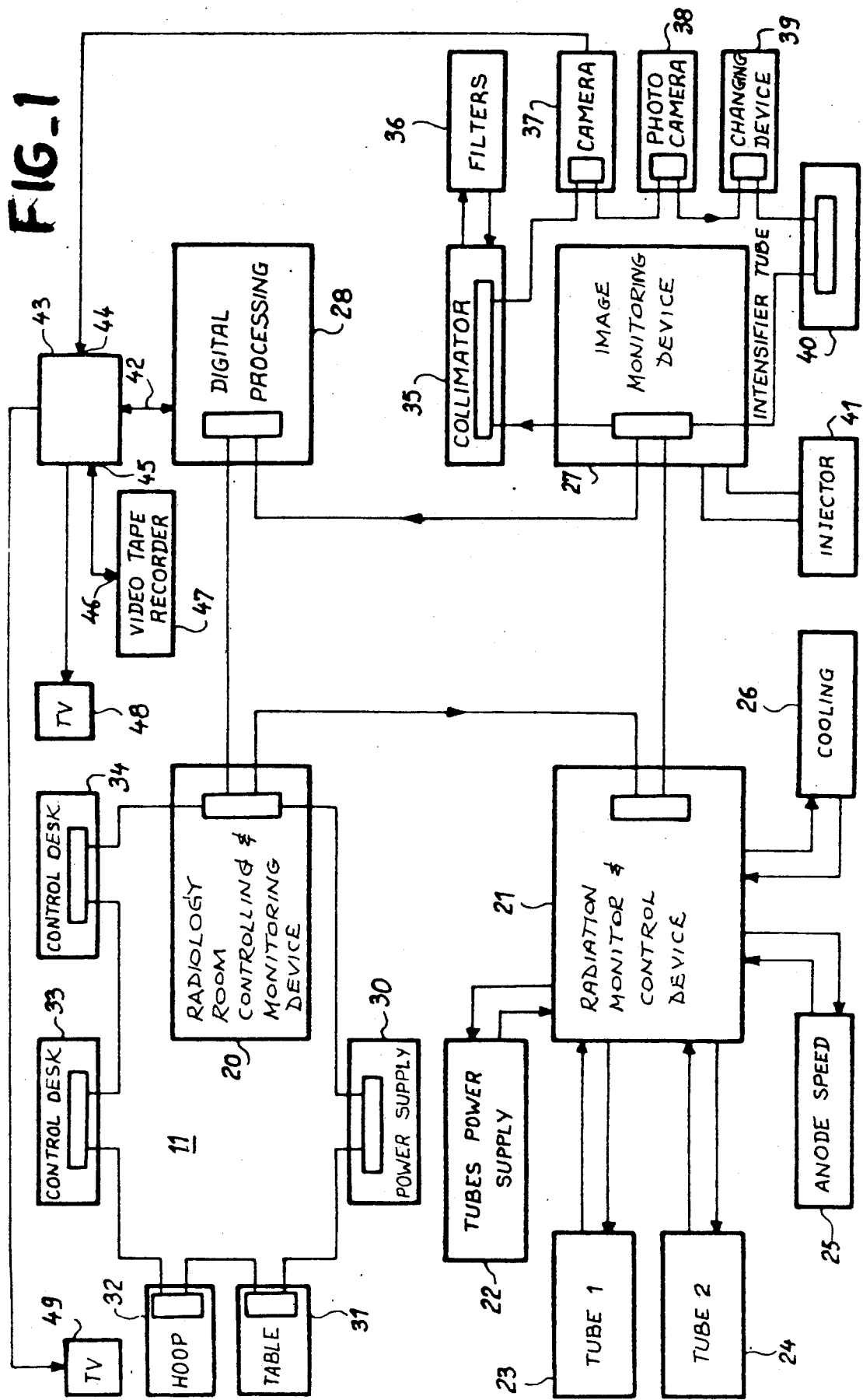
FIG_1

FIG_2
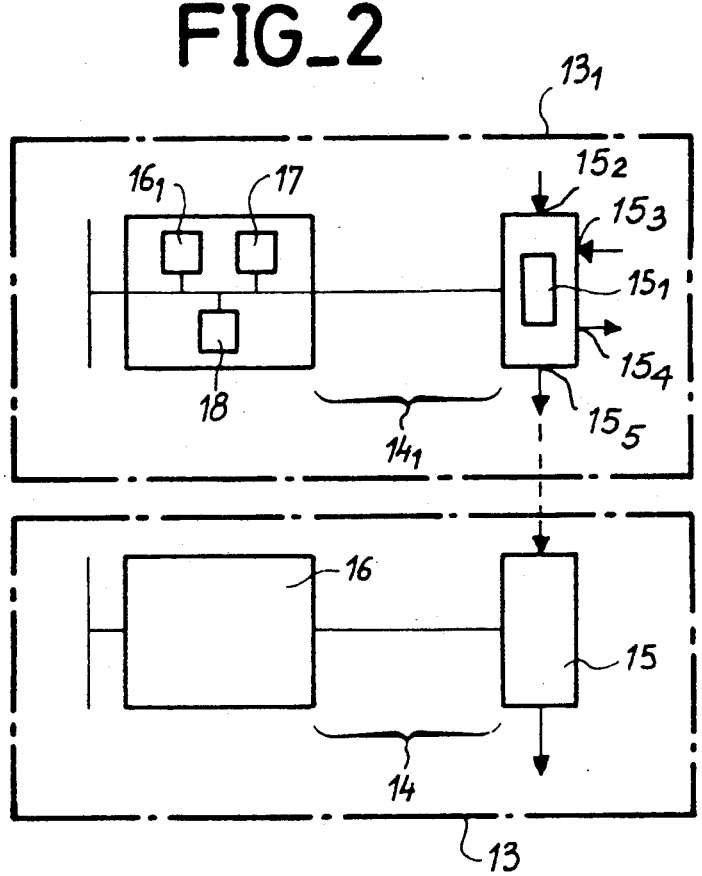
FIG_3
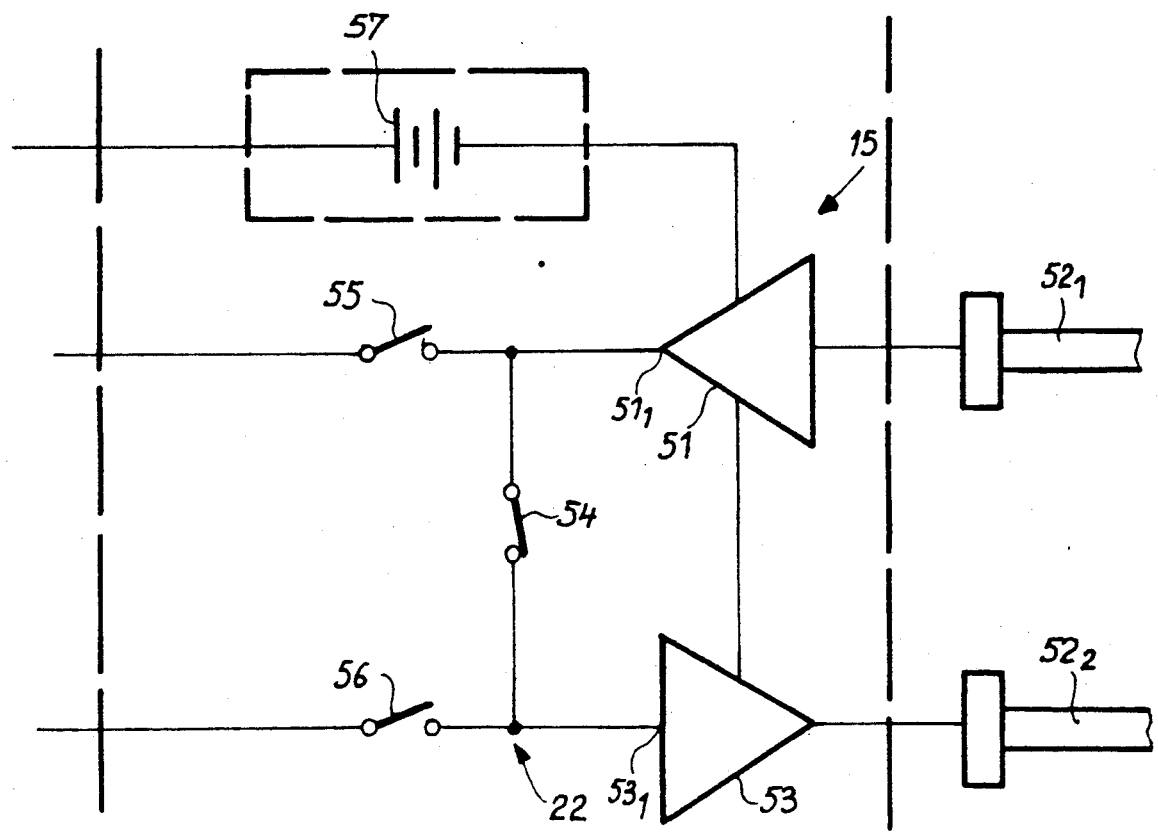

FIG_4
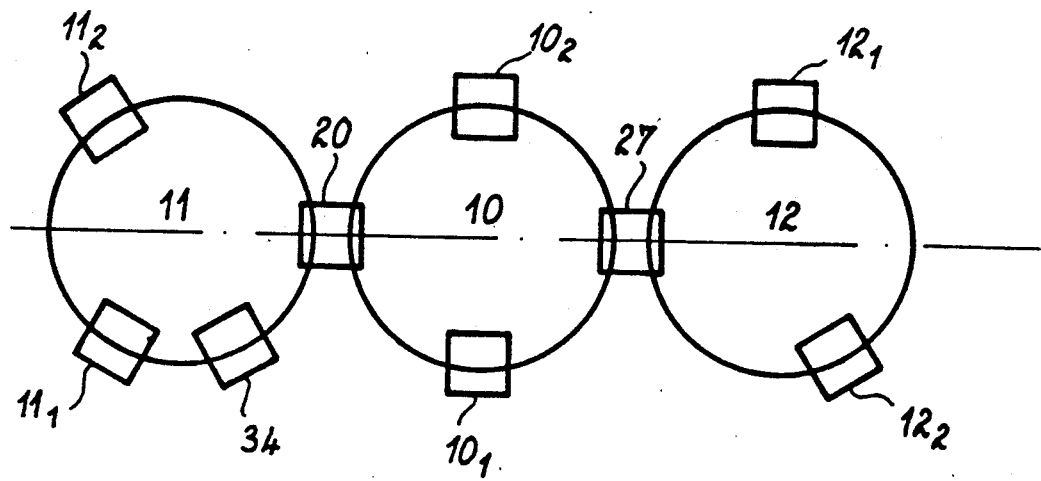

RADIOLOGY INSTALLATION WITH A COMMUNICATIONS NETWORK

This application is a continuation of application Ser. No. 045,872, filed on May 4, 1987, now abandoned.

BACKGROUND OF THE INVENTION

1. Field of the Invention

The invention pertains to a radiology installation.

A radiology installation, especially for radioscopy or radiography comprises a large number of instruments which are connected with one another according to requirements. For example, for radioscopy, an X-ray generator, an image intensifier tube, a video camera and a television receiver or monitor are used; for radiography, instead of a video camera and a television monitor, a photographic camera with a film-changing device. When a specified type of examination is being made, a number of instruments are put into operation while the others are out of action, and special connections are set up among the instruments in operation. Thus, for each type of use, the installation is given a specified configuration. To make it possible to change the configuration instantaneously, the installation is often provided with a complex wiring system.

2. Description of the Prior Art

To simplify the assembly, a radiology installation has been proposed in which the X-ray generator is connected with the other instruments in a closed loop where the data is transmitted from one instrument to another by means of an optic fiber. When an instrument is not used or when it has failed, the information is shunted by a change-over switch so as to keep the loop closed.

This installation of the prior art has limitations which can entirely eliminate the advantage gained by simplified wiring. It has been especially observed that when there is a large flow of data to be transmitted between two instruments, the line forming the enclosed loop may be saturated and may simultaneously prevent a large flow of data among other instruments.

3. Summary of the Invention

The invention removes these disadvantages.

According to the invention, the data signals among the instruments of the installation flow along at least two loops which are connected to each other. With an installation of this type, the data can flow simultaneously at a high rate in two distinct loops, and two instruments located in two different loops can be made to communicate with each other.

For example, an image-processing operation recorded in a digital processing instrument may require an exchange of data at a high rate between a control desk and this instrument. This is especially so in the use of a dialogue device such as a tactile screen, a "mouse" or a joystick. With the invention, if the controls of the camera, the image intensifier tube and the image collimator are in a separate loop from the one in which the digital processing instrument is located, it is possible to perform a radiographic operation at the same time as an image processing operation.

In one embodiment, there is provision for a main loop to which the secondary or specialized loops are connected.

In this case, it is possible to assign, to each secondary loop, a monitoring and control device for all the instruments of this loop, this device being at the node between the secondary loop and the main loop.

A secondary loop comprises, for example, the positioning controls for the instruments in the radiology room, namely the patient-bearing and the support, generally hoop-shaped, of the unit formed by the X-ray tube and the detectors. Another secondary or specialized loop is assigned to the control of the image-forming devices such as a photographic camera or a video camera.

For an installation according to the invention, the use of an HDLC (high level data link control) type of communications protocol has been found to be particularly advantageous.

To make the installation of the invention, in one example, a communications and processing device is assigned to each instrument, and this device comprises, separately, a device for handling communications with the other instruments and a circuit for processing messages intended for the instrument or coming from the instrument.

The communications-handling circuit is, for example, a circuit comprising a change-over switch made up of a single switch in parallel which closes when a hitch is detected in the corresponding instrument.

The signals in each loop are of the electrical or optical type.

In the preferred embodiment of the invention, a loop, known as the main loop, has a central handling unit which, whenever the installation becomes powered, determines the configuration of this installation, i.e. it determines the loop in which each instrument is placed and retains this configuration in memory, this determining operation being performed with the help of ancillary handling units, which are located at the junctions between the neighboring loops and which transmit, to the central handling unit, the list of instruments connected to the loop that is furthest from the main loop.

With an installation of this type, the communications path between two instruments is determined automatically at each use, without its depending on the connection. For, when a first instrument in a first loop has to communicate with a second instrument in a second loop, which is distinct from the first one, the first instrument is made to transmit a message on its loop and this message is received by the ancillary handling unit of this loop, which memorizes the configuration of the first loop and that of the neighboring loop and which thus directs the message towards this neighboring loop. If the second instrument is not in this neighboring loop, the message is transmitted by other ancillary handling units to the nodes between this neighboring loop and another loop, and so on until the second loop and the second instrument are reached.

Furthermore, with a communications and processing device assigned to each instrument as well as with a central handling unit and ancillary handling units at each node, the communications and processing device of each instrument may be of an identical nature for all the instrument, namely it may be independent of the type of instrument and the configuration of the installation, thus providing not only for lower costs but also for modifying the configuration by simple modifications of the connections between instruments without any other modifications since, as indicated above, the configuration is determined whenever the power is turned on and the communications path between instruments is set up automatically.

BRIEF DESCRIPTION OF THE DRAWINGS

Other characteristics and advantages of the invention will emerge from the description of certain of its embodiments, this description being made with reference to the appended drawings, of which:

FIG. 1 is a diagram of an installation according to the invention,

FIG. 2 is a diagram of a communications device associated with each instrument of the installation of FIG. 1, FIG. 3 depicts a specific feature of the device of FIG. 2, and FIG. 4 is a simplified diagram corresponding to FIG. 1, enabling a better understanding of the working of the installation.

DETAILED DESCRIPTION OF THE INVENTION

The radiology installation shown in FIG. 1 can be used for radioscopic or radiographic examinations as well as for the digital processing of images.

The messages (control or status data) are transmitted through communications lines which are formed of optic fibres and organized in several loops with a main loop 10 and two secondary loops 11 and 12.

As can be seen in FIG. 2, with each instrument 13, there is an associated communications device 14 comprising, firstly, a circuit 15 to handle signals communications among instruments and, secondly, a circuit 16 to process data which is intended for or comes from the instrument 13 as such. Each circuit has a microprocessor-based computing means. For the communications-handling circuit 15, the central processing unit of the microprocessor bears the reference $15_1$ while, for the circuit 16, the central processing unit of the microprocessor bears the reference $16_1$. This circuit 16 further comprises a memory 17 and a circuit 18 for the handling of parallel inputs/outputs.

The instruments located at a node, such as the one with the reference $13_1$ in FIG. 2, which are between the main loop 10 and a secondary loop 11 or 12, are associated with communications devices $14_1$, comprising a communications-handling circuit with two inputs $15_2$ and $15_3$ and two outputs $15_4$ and $15_5$.

The instruments that have their controls on the main loop 10 are:

A radiology room controlling and monitoring device 20 which is also in the secondary loop 11, known as the room loop, A radiation monitor and control device 21 to monitor and control the X-radiation power: this device controls and monitors a tubes power supply 22 which supplies electrical power to two X-ray tubes 23 and 24, an anode speed device 25 that controls the rotation speed of the rotating anode of each tube, 23, 24, and a cooling device 26, An image monitoring device 27 for monitoring images, which is also in the secondary loop 12, known as the image loop, And a digital processing device 28 for the digital processing of images.

The secondary radiology room loop 11 has, after the device 20, a device 30 for controlling the electrical power supply to the instruments of the radiology and for the lighting of this room, the controls 31 for positioning the table that bears the patient, the controls 32 for positioning a hoop bearing the X-ray tubes and the detector(s), a control desk 33 in the radiology room near the table that bears the patient and a general control desk 34.

The secondary image loop 12 has, after the image monitoring device 27, the control of collimator 35 associated with contour filters 36, the control of a video camera 37, the control of a photographic camera 38, the control of a film-changing device 39 and the control of an image intensifier tube 40. Furthermore, a device 41 for the automatic injection of contrast product into the blood vessels of the patient is directly controlled by the device 27.

The digital processing device 28 can be used to conduct so-called "subtractive" imaging in which the difference is obtained, point by point, between the luminance values given at each point with a contrast product and the luminance values given at each point without a contrast product. This imaging method is used especially for the examination of blood vessels (known as angiography).

The device 28 is linked, by a line 42, to a video distribution circuit 43 that has an input 44 receiving the signal from the camera 37 and an input/output 45 linked to an input/output 46 of a video tape recorder 47. The circuit 43 further comprises two outputs linked to two television monitors, 48 and 49, the former being placed near the central control desk 34 and the latter near the table that bears the patient.

In the main loop 10 and in the secondary loops 11 and 12, the data is transmitted from one instrument to another by optic fibers. Thus, at the input of the circuit 15 (FIG. 3) it is planned that there will be a converter 51 which converts a light signal, transmitted by an optic fiber $52_1$, into an electrical signal and, at the output of this circuit 15, there is a converter 53 which transforms an electrical signal that comes from this circuit or is conveyed by this circuit into a light signal sent towards an optic fiber of the output $52_2$.

The output $51_1$ of the input converter 51 is directly connected to the input $53_1$ of the output converter 53 by means of a switch 54 which is open in normal operation but is closed in the event of a hitch in the corresponding instrument, so that the corresponding loop remains closed despite the hitch. The switch 54 can also come into action when the corresponding instrument is not used.

Set in series with the output conductor of the converter 51, there is another switch 55. Similarly, connected in series with the input conductor 53, there is a switch 56. The switches 55 and 56 are closed during normal operation and opened in the event of hitches An electric battery 57 supplies electrical energy to the converters 51 and 53 so that the signal can be transmitted even if the usual power supply to the corresponding instrument 13 is interrupted.

The characteristics of the installation of FIG. 1 will be better understood through a description of an example of the use of this installation. This example pertains to radiography, i.e. to the use of the photographic camera 38.

The operator presses a button on the control desk 34 to give a command for a radiographic examination. This command is transformed into a message conveyed by the circuits 16 and 15, associated with this control desk, towards the room monitoring device 20 which, based on the message received, prepares another message determining the path that must be followed by the messages, this latter message being used as the actuating or stopping command by the various instruments of the installation. Thus, in the secondary loop 11, the message from the power supply desk 34 is interpreted by the control 30 as a command for starting up or maintaining the electrical power supply in the room. However, it is through the messages previously sent by the control desk 33 that the table 31 and the hoop 32 supporting the X-ray source and the detector(s) have been placed in the desired position.

The message of the device 20 is transmitted in the main loop 10, firstly to the device 21 which prepares a configuration for the use of the X-ray sources and, secondly, to the device 27 for monitoring images which, in the secondary loop 12, also prepares a configuration of use.

The device 21 determines which of the two tubes, 23 or 24, are to be used. For example, if the tube 23 has functioned shortly before, only the tube 24 is used. The rotational speed of the rotating anode is determined at the value corresponding to the radiography, i.e. in this example, 900 rpm. If necessary, the cooling device 26 is started up and the power supplying means for the tubes are kept on stand-by pending the final command to start taking shots.

In the secondary loop 12, all the instruments, with the exception of the television camera, are kept on stand-by. The message is retransmitted to the device 20 through the device 28 for the digital processing of images which, in this case, is not used.

The message retransmitted to the device 20 indicates whether the operation is correct or not. If there is a positive response, an indication is given at the control desk 34 and the operator can then give the final command for taking shots. As an alternative, a prohibiting indication is given to the operator if there is a hitch and the absence of a prohibition signifies permission for taking shots.

The configuration of the system in a main loop and secondary loops provides greater possibilities then could be obtained if all the data were to flow through a single loop. For example, the data in the loop 12 does not go through the main loop 10 and therefore, does not risk saturating the flow of data in this main loop. Reciprocally, the data in the loop 12 can flow without delay despite there being a large quantity of data in the loop 10. In this way, it is possible, for example, to perform a radiography while, at the same time, processing images, by means of the control desk 34 and the devices 28 and 43, for a radioscopy conducted earlier. For an image processing operation of this type can entail a great flow of data in the loop 10 if a tactile screen, a mouse or a joystick are used at the control desk to draw lines on the image.

FIG. 4 gives a simplified view of the three loops 10, 11 and 12 with the device 20 connecting the loops 10 and 11 and the device 27 connecting the loops 10 and 12. In the loop 11, there is the central control desk 34 and the devices $11_1$, $11_2$ etc. In the device 10, there are the instruments $10_1$, $10_2$, etc. and in the loop 12, the references $12_1$, $12_2$ refer to the instruments in this loop. This simplified loop can provide for a better understanding of the other specific features of the installation and its operation.

When the power is turned on in the installation each time that it is used, the device 20 forms the main handling unit which determines the configuration of this installation. For this purpose, this device 20 sends a message in the loop 11 and each handling and communications device associated with each instrument that receives a message, sends back, to this device 20, a message indicating that the control desk 34 and the instruments $11_1$ and $11_2$ are in this loop 11. The device 20 retains this data in memory. It also sends a message to the loop 10. The instruments $10_1$ and $10_2$, as well as the device 27 indicate that they are on the loop 10 and this data is kept in memory by the device 20. The device 27 sends the message asking for a configuration to the loop 12 which indicates the presence of the instruments $12_1$ and $12_2$, and this information on the instruments $12_1$ and $12_2$ in the loop 12 is retransmitted by the same device 27 to the central device 20. On the basis of this information, the device 20 can determine the optimum path between one instrument and another. For example, for communication between the instruments 111 and $12_1$, the data must flow through the devices 20 and 27.

Furthermore, it is possible to assign the main installation-controlling role to the device 27, at least for certain operations. For example, for preparing a radiological examination, the device 20 comprises, as described, the central control unit. By contrast, during the acquisition of images, it is the device 27 which constitutes the central controlling unit, i.e. its messages have priority. In other words, a command given by the device 27, when it is a central control organ, prevails over an command given by the device 20. Of course, this exchanging of rules is done not by a physical alteration of the installation but by the prior programming of the monitoring and control devices.

The configuration of the installation can be easily modified For example, if a communication has to be permanently established between the instruments $11_1$ and $12_1$, they can be arranged in the same loop. The connections are then modified, for example by taking the instrument $12_1$ into the loop 11 without any other modification being needed. For, since the configuration is regularly checked, it is automatically taken into account by the various monitoring and control devices.

It must be noted that this configuration is determined not only whenever the power is turned on but also whenever there is a fault or a hitch detected in an instrument.

What is claimed is:

1. A radiology installation, comprising:
a first plurality of instruments for using images produced from x-ray radiation which are connected in series to form a closed primary loop in which primary loop data flows between said first plurality of instruments;
a second plurality of instruments for using images produced from x-ray radiation which are connected in series to form a closed secondary loop in which secondary loop data flows between said second plurality of instruments;
controlling and monitoring means connecting to said closed primary loop and said closed secondary loop for controlling and monitoring said closed primary loop and said closed secondary loop and for coordinating communications between said closed primary loop and said closed secondary loop which are otherwise independent of each other; and
said controlling and monitoring means comprises a central handling unit which has a memory, said central handling unit having means for determining a configuration of said radiology installation so that a location of each instrument of said first plurality of instruments and a location of each instrument of said second plurality of instruments is registered in said central handling unit's memory;

and an ancillary handling unit, said ancillary handling unit having means for transmitting a message from an instrument located in said first plurality of instruments to an instrument located in said plurality of instruments, said ancillary handling unit being located at a junction which connects said primary and secondary loops.

2. An installation according to claim 1, wherein:
said first plurality of instruments of said primary loop comprise a radiation monitor and control device, a digital processing device, an image monitoring device, and said controlling and monitoring device connected in series.

3. An installation according to claim 1, wherein:
said first plurality of instruments of said secondary loop comprise a power supply, table-positioning controls, a table for a patient, and a hoop bearing X-ray tubes and detectors, and a general control desk connected in series.

4. An installation according to claim 1, wherein:
each instrument of said plurality of instruments in said primary loop and said secondary loop has a communication device comprising an information circuit that processes information for said each instrument and a transmission circuit designed for the transmission of messages, said transmission circuit being connected between said information circuit and a connecting means connected to one of the loops consisting of said primary and secondary loops.

5. An installation according to claim 4, wherein:
said each instrument comprises a switch which is closed when problems arise in said each instrument so that the loop in which said each instrument is placed remains closed.

6. An installation according to claim 4, wherein:
said messages are transmitted by optical fibers, and said transmission circuit for the transmission of messages converts light into electrical signals at its input and converts electrical signals into light at its output.

7. An installation according to claim 1, wherein:
identical communication and processing devices are associated with each instrument of said plurality of instruments of said primary loop and said secondary loop.

8. A radiology installation, comprising:
a first plurality of instruments, for using images produced from x-ray radiation which are connected in series to form a closed primary loop in which primary loop data flows between said first plurality of instruments;

a second plurality of instruments for using images produced from x-ray radiation which are connected in series to form a closed secondary loop in which secondary loop data flows between said second plurality of instruments;

a third plurality of instruments for obtaining images produced from x-ray radiation which are connected in series to form a closed second secondary loop in which second secondary loop data flow between said third plurality of instruments;

controlling and monitoring means connected to said primary loop and said secondary loop for controlling and monitoring said primary loop, and for coordinating communication between said primary loop, said secondary loop and said second secondary loop which are otherwise independent of each other;

said controlling and monitoring means comprises a central handling unit which has a memory, said central handling unit having means for determining a configuration of said radiology installation so that a location of each instrument of said first plurality of instruments, said second plurality of instruments, and said third plurality of instruments is registered in said central handling unit's memory; and a first ancillary handling unit which connects said primary and said secondary loops and a second ancillary handling unit which connects said primary and said second secondary loops, said first and second ancillary handling units having means for transmitting messages between any of said instruments located in said primary, secondary and second secondary loops.

9. An installation according to claim 8, wherein:
said plurality of instruments of said second secondary loop comprise a collimator, a video camera, a photographic camera, a film-changing device and an image intensifier tube.

10. An installation according to claim 8, wherein:
said first plurality of instruments of said primary loop comprise a radiation monitor and control device, a digital processing device, an image monitoring device, and said controlling and monitoring device connected in series.

11. An installation according to claim 8, wherein:
said plurality of instruments of said secondary loop comprise a power supply, table-positioning controls, a table for a patient, and a hoop bearing X-ray tubes and detectors, and a general control desk connected in series.

12. An installation according to claim 8, wherein:
each instrument of said plurality of instruments in said primary loop, said secondary loop, and said second secondary loop has a communication device comprising an information circuit that processes information for said each instrument and a transmission circuit for the transmission of messages said transmission circuit being connected between said information circuit and a connecting means connected to one of the loops consisting of said primary, secondary and second secondary loops.

13. An installation according to claim 12, wherein:
each instrument comprises a switch which is closed when problems arise in said each instrument so that the loop in which said each instrument is placed remains closed.

14. An installation according to claim 8, wherein:
said messages are transmitted by optical fibers, and said transmission circuit for the transmission of messages converts light into electrical signals at its input and converts electrical signals into light at its output.

15. An installation according to claim 8, wherein:
identical communication and processing devices are associated with each instrument of said plurality of instruments of said primary loop, said secondary loop and said second secondary loop.

* * * * *